United States Patent [19]

Howard

[11] 4,230,535
[45] Oct. 28, 1980

[54] HEAT-PUMPED FRACTIONATION PROCESS

[75] Inventor: Leroy J. Howard, Libertyville, Ill.

[73] Assignee: UOP Inc., Des Plaines, Ill.

[21] Appl. No.: 48,859

[22] Filed: Jun. 15, 1979

[51] Int. Cl.² .................... B01D 1/28; B01D 3/14
[52] U.S. Cl. ................... 203/26; 203/DIG. 4;
203/DIG. 9; 62/26; 62/31; 202/185 A;
585/800
[58] Field of Search ............... 203/26, 24, 100, 42,
203/DIG. 4, DIG. 9, 87; 62/24–28, 30, 31;
585/800; 202/185 A, 182, 183, 184

[56] References Cited

U.S. PATENT DOCUMENTS

| 2,534,274 | 12/1950 | Kniel | 203/26 |
|---|---|---|---|
| 3,187,066 | 6/1965 | Nathan | 203/26 |
| 3,230,155 | 1/1966 | Schürch | 203/26 |
| 3,414,484 | 12/1968 | Carson et al. | 203/26 |
| 3,418,215 | 12/1968 | Nirenberg | 203/26 |
| 3,568,457 | 3/1971 | Briggs et al. | 203/26 |
| 4,137,129 | 1/1979 | Bjorklund | 203/26 |

FOREIGN PATENT DOCUMENTS 659886 3/1963 Canada ........................... 16/26

OTHER PUBLICATIONS

The Oil and Gas Journal, Wolf, C. W. et al. Sep. 1, 1975 p.p. 85–88.

Primary Examiner—Wilbur L. Bascomb, Jr.
Attorney, Agent, or Firm—James R. Hoatson, Jr.; John F. Spears, Jr.; William H. Page, II

[57] ABSTRACT

A process for separating two close-boiling chemical compounds by fractionation wherein a vapor stream removed from the overhead receiver is superheated by indirect heat exchange and is then further heated by compression. The thus-heated high pressure stream is cooled by heat exchange against the overhead vapor and split into at least two portions. One portion of the high pressure stream is passed through a reboiler at an intermediate point in a fractionation column. Preferably, both portions of the high pressure stream are subcooled and returned to the overhead receiver except for the overhead product drawn off.

14 Claims, 1 Drawing Figure

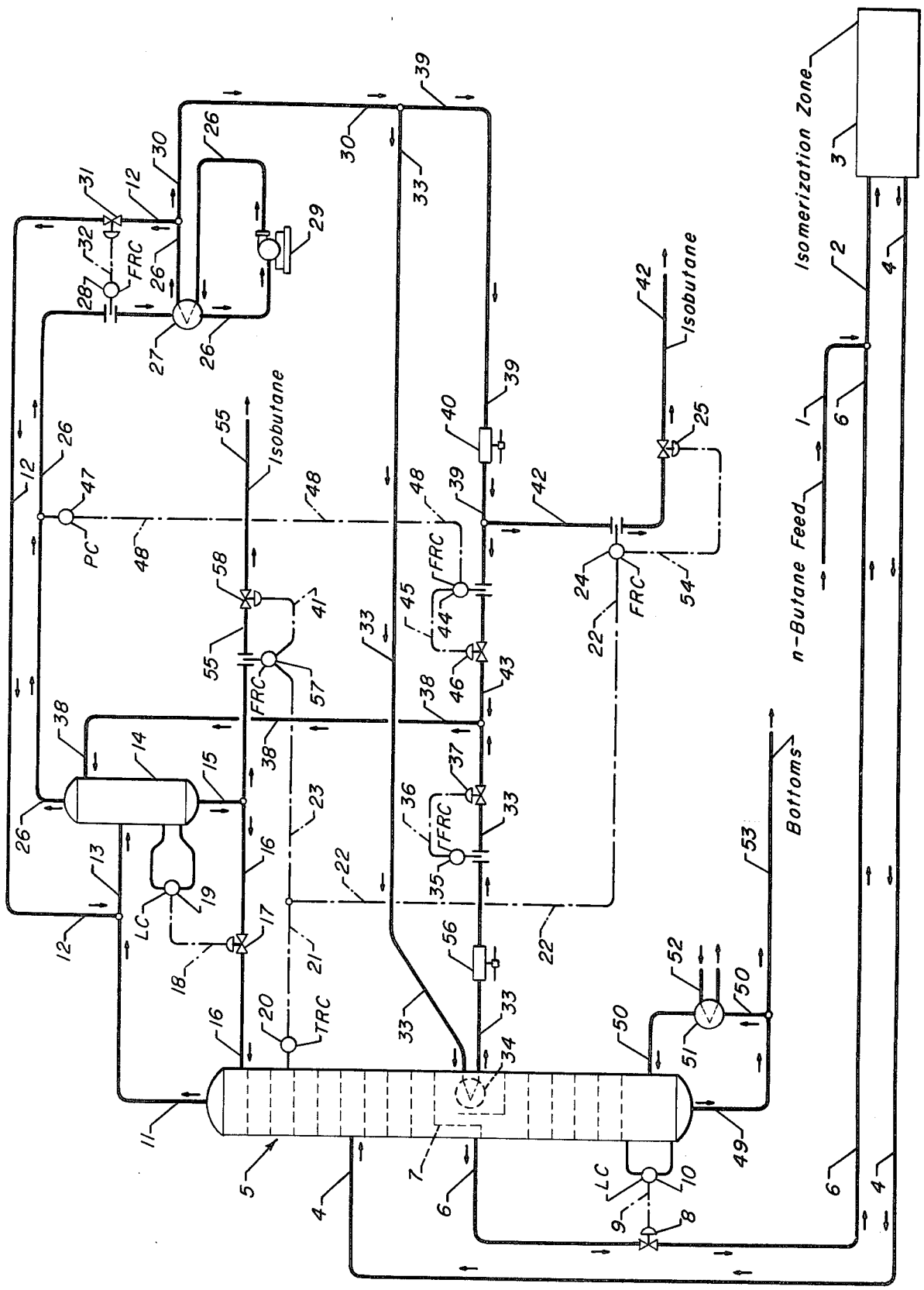

HEAT-PUMPED FRACTIONATION PROCESS

FIELD OF THE INVENTION

The invention relates to a process for separating two close-boiling chemical compounds by fractionation. The invention more specifically relates to a process for fractionating a mixture of two close-boiling hydrocarbons. The invention also relates to the use of heat pumps in the fractionation of hydrocarbons. References concerned with similar subject matter are found, for instance, in Classes 55, 62 and 203.

PRIOR ART

The separation of hydrocarbons by fractionation is an old and well developed art. Those skilled in the art have recognized that in certain situations heat pumps may be used to advantage to reduce the utilities cost of operating a fractionation process. This recognition has led to the utilization of a heat pump to reboil the bottom of a fractionation column by the indirect heat exchange of bottoms liquid and compressed overhead vapors of the same column. Separatory processes utilizing this are presented in U.S. Pat. No. 3,230,155 issued to R. Schurch and U.S. Pat. No. 3,414,484 issued to D. B. Carson (both Cl. 203-26). In these prior art systems, the overhead vapor is compressed to raise its temperature and is then passed into the reboiler located at the bottom of the column. The indirect heat exchange in the reboiler causes the condensation of at least some of the overhead vapor to produce overhead liquid. This liquid is used as reflux and removed as a product. The heat exchange also vaporizes a portion of the bottoms liquid to reboil the column. A similar system in which a separate refrigerant liquid is used to transfer heat removed in condensing the overhead vapors to the reboiled liquid is shown in U.S. Pat. No. 2,534,274 issued to L. Kniel.

U.S. Pat. No. 3,568,457 (Cl. 62-28) issued to T. M. Briggs et al presents a process for fractionating propylene and propane in which the overhead vapor stream is passed into an overhead receiver. Vapor removed from the overhead receiver is heated by compression. One portion of the heated overhead vapor stream is used to reboil the bottom of a fractionation column while a second portion is passed through a cooler. The resulting liquid streams are then passed into the overhead receiver.

U.S. Pat. No. 4,137,129 (Cl. 203-26) issued to B. L. Bjorklund also presents a heat pumped process for fractionating hydrocarbons. This process provides a cool fluid for condensing the overhead vapor stream by flashing the bottoms liquid of the column. The column is reboiled by compressing vapor formed in flashing the bottoms liquid and in cooling the overhead vapor stream.

Conventional methods of utilizing a heat pump in a fractionation process are also described in some detail in the article starting at page 85 of the Sept. 1, 1975 edition of the *Oil and Gas Journal*. The article is directed to the use of heat pumps in conjunction with other aids, such as enhanced heat transfer reboiler tubing and high liquid loading trays, to conserve energy normally expended in the fractionation of close-boiling compounds. The article also presents a high efficiency system in which a trim compressor and trim condenser are used to remove heat from a previously compressed portion of the overhead vapor. Specific examples of the use of the process are the separation of propylene and propane; butene-2 and isobutane; and ethylene and ethane.

The use of heat pumps in the fractionation of light hydrocarbons is also described in an article appearing at page 96 of the Feb. 9, 1976 edition of the *Oil and Gas Journal*. In one of the processes described, the overhead vapor stream is admixed with flash vapor and then compressed. The resultant hot vapor is used to reboil the fractionation column and is then flashed into the overhead receiver.

It is believed these references describe the prior art use of heat pumps in fractionation processes.

BRIEF SUMMARY OF THE INVENTION

The invention provides an energy efficient process for separating two close-boiling chemical compounds by fractional distillation. The preferred embodiment of this process may be broadly characterized as comprising the steps of passing a feed stream comprising a first and a second hydrocarbon which have the same number of carbon atoms per molecule into a fractionation zone at a first intermediate point; removing a net bottoms stream, which is rich in the first hydrocarbon, from the fractionation zone as a first product stream; removing an overhead vapor stream which is rich in the second chemical compound from the fractionation zone, partially condensing the overhead vapor stream by direct heat exchange within an overhead receiver to produce overhead liquid and a receiver vapor stream, and supplying the overhead liquid to the fractionation zone as reflux; heating the receiver vapor stream by indirect heat exchange against a high pressure working stream; further heating the receiver vapor stream by compression and thereby forming the high pressure working stream; cooling the high pressure working stream by the indirect heat exchange against the receiver vapor stream; passing a first portion of the high pressure working stream through a first reboiler used to supply heat to the fractionation zone at a lower second intermediate point and condensing the first portion of the high pressure working stream; condensing a second portion of the high pressure working stream; withdrawing part of the condensed second portion of the high pressure working stream from the process as a second product stream which is rich in the second hydrocarbon; and passing the condensed first portion and the remainder of the condensed second portion of the high pressure working stream into the overhead receiver.

In another embodiment of the invention, a portion of the overhead liquid is withdrawn from the process as the second product stream.

There is also presented a novel control system and a novel process control method for use on heat-pumped fractionation processes.

DESCRIPTION OF THE DRAWING

The Drawing illustrates the preferred embodiment of the invention. For clarity and simplicity, various subsystems and apparatus associated with the operation of the process have not been shown. These items include pumps, fractionator internals and some flow and pressure control systems, etc., which may be of customary design and manufacture. This representation of the preferred embodiment is not intended to preclude from the scope of the invention those other embodiments set out herein or which are the result of reasonable and normal modification of these embodiments.

Referring now to the Drawing, a feed stream of relatively pure normal butane enters the process in line 1. This feed stream is admixed with a recycle liquid stream carried by line 6 and passed into a catalytic butane isomerization zone 3 through line 2. This isomerization includes a reaction zone effluent vapor-liquid separator and a stripping column. The stripped effluent stream of the isomerization zone comprises a mixture of iso- and normal butanes and is carried by line 4 to an upper intermediate point of a fractionation column 5. A portion of the heat necessary for the fractionation process is supplied to the bottom of the fractionation column 5 by a reboiler 51 which receives heat from a hot fluid circulated through line 52.

A bottoms liquid stream is removed from the bottom of the fractionation column 5 in line 49 and divided into a first portion which passes through the reboiler and reenters the bottom of the fractionation column through line 50 and a second portion which is withdrawn as a net bottoms product through line 53. This relatively small stream contains higher boiling impurities such as pentane which are present in the normal butane feed stream. A sidecut liquid stream is removed from the fractionation column in line 6 at a rate controlled by valve 8 and is then passed into the isomerization zone as the recycle liquid stream. Valve 8 receives an operating signal through means 9 from a level controller 10 which monitors the liquid level at the bottom of the fractionation column.

An overhead vapor stream which is rich in isobutane is removed from the top of the fractionation column 5 in line 11. This vapor stream is admixed with a spilled-back mixed-phase fluid stream from line 12 and is then passed into an overhead receiver 14 through line 13. The overhead vapor stream is partially condensed within the overhead receiver by direct heat exchange with cool liquid which enters the overhead receiver through line 38. The liquid which collects in the bottom of the overhead receiver 14 is withdrawn through line 15. In one embodiment of the subject invention, all of the liquid flowing through line 15 is passed into line 16 and supplied to an upper portion of the fractionation column as reflux. The rate of flow of the reflux liquid to the column is controlled by valve 17 in response to a signal carried by means 18 from a level controller 19 which monitors the liquid level in the overhead receiver. When all of the liquid which is removed from the overhead receiver 14 is returned to the column as reflux, the net isobutane produced in the process is withdrawn through line 42.

The vapor which is present in the overhead receiver is withdrawn through line 26 as the receiver vapor stream and passed through an indirect heat exchange means 27 wherein it is heated. The receiver vapor stream is then passed through a compressor 29 which functions as a heat pump and which further increases the temperature of the receiver vapor stream. The receiver vapor stream continues through line 26 and passes through the indirect heat exchange means 27 wherein it is cooled to a temperature between those maintained in the overhead receiver and at the discharge of the heat pump. The high temperature effluent of the heat pump is also referred to herein as the high pressure working stream. A small portion of this high pressure working stream is allowed to return to the overhead receiver through line 12 at a rate controlled by valve 31. This valve is actuated in response to a signal carried by means 32 from a flow controller 28. This small flow is maintained basically for the purpose of smoothing out the operation of the control system and increasing the controllability of the valves used in the system.

The major portion of the high pressure working stream is passed through line 30. Part of the material flowing through line 30 is diverted into line 33 and passed through a stabbed-in reboiler 34. The total downward liquid flow within the fractionation column is trapped off at downcomer 7 and spills into the reboiler tub in which the reboiler 34 is located. A major portion of the heat required for the separation of the isobutane product from the normal butane which is recycled to the isomerization zone is supplied by the high temperature vapors passed through line 33. A portion of this stream is preferably condensed in giving up heat in the reboiler to form a mixed phase stream which is passed into a cooler 56. The material in line 33 is condensed in the cooler and is also preferably subcooled. The fluid flow through line 33 is controlled by a valve 37 in response to a signal carried by means 36 from a flow controller 35.

A second portion of the high pressure working stream flowing through line 30 is passed through line 39. The material in line 39 is passed into a cooler 40 which is also referred to herein as a trim condenser. The effluent of cooler 40 is carried by line 39 and is a high purity stream of isobutane. When the total hydrocarbon liquid present in the overhead receiver is to be returned to the fractionation column as reflux, a portion of the isobutane stream flowing through line 39 is removed in line 42 as the net overhead product stream removed from the fractionation column. The rate of flow of this stream is controlled by a valve 25 in response to a signal carried by a means 54 from a flow controller 24. The set point of this flow controller is periodically reset as required by a signal carried by means 22 and 21 from a temperature controller 20.

The portion of the isobutane flowing through line 39 which is not removed in line 42 is carried by line 43. The flow rate of the liquid in line 43 is set by valve 46 in response to a signal carried by means 45 from a flow controller 44. The set point of this flow controller is periodically adjusted as required in response to a signal carried by means 48 from a pressure controller 47. The flow rate of the preferably subcooled isobutane through line 43 is thereby used to control the overhead pressure in the fractionation system. The material flowing through line 43 is admixed with the liquid from line 33 and passed into the overhead receiver through line 38. The passage of this low temperature liquid into the overhead receiver effects the partial condensation of the overhead vapor stream.

In a second embodiment of the invention, a portion of the overhead liquid which is withdrawn from the overhead receiver through line 15 is passed through line 55 and removed as the net overhead product. In this embodiment of the invention, there is no fluid flow through line 42. The temperature controller 20 transmits a signal through means 21 and 23 which adjusts as required the setpoint of a flow controller 57. Flow controller 57 transmits a signal through means 41 to a flow control valve 58 which regulates the flow of the net overhead product through line 55.

DETAILED DESCRIPTION

The constantly increasing cost of energy has prompted renewed emphasis on the development of energy-efficient petroleum and petrochemical processes. One of the energy-consuming operations performed in many of these processes is the separation of two chemical compounds by fractionation. It is an objective of this invention to provide a highly energy-efficient fractionation process for such separations. It is another objective of the invention to provide a fractionation process for the separation of close-boiling chemical compounds using a heat pump. It is yet another objective of the invention to provide an energy-efficient process for separating light hydrocarbons having the same number of carbon atoms per molecule by fractionation.

The subject process may be applied to processes for the separation of a great many chemical compounds. The close-boiling chemical compounds in the fractionation zone feed stream may comprise inorganic chemicals, inorganically substituted organic chemicals or hydrocarbons. The feed stream may therefore comprise halogenated hydrocarbons, alcohols, ethers, ketones, olefins, paraffins or aromatics. The use of a heat pump on a fractionation column is normally restricted to use with relatively close-boiling compounds. The compounds to be separated therefore preferably have boiling points which are no more than 20 Fahrenheit degrees apart at the pressure imposed in the fractionation column. A better statement of this criteria is that the separation of the two compounds is difficult due to the vapor-liquid equilibrium ratios or K's of the two compounds being close to the same value, or that $\alpha$, the relative volatility of the system, is close to unity. This situation indicates the need for a high reflux ratio and results in high utility costs for the separation.

The close-boiling chemical compounds separated in the subject process are preferably light hydrocarbons. As used herein, the term "light hydrocarbons" is intended to indicate a hydrocarbon having less than seven carbon atoms per molecule. More preferably, the close-boiling chemical compounds are hydrocarbons having either three or four carbon atoms per molecule. Examples of the pairs of compounds which may be separated in the subject process are ethane and ethylene; propane and propylene; butane and various butylenes; isobutane and n-butane; and isopentane and n-pentane. The feed stream to the subject process is preferably a stripped hydrocarbon stream which contains substantially no components which are lighter (more volatile) than the lightest of the two hydrocarbons which are being separated. In this context, the phrase "substantially no" or similar phrases is intended to indicate a concentration of less than 1.0 mole percent. The feed stream may contain substantial amounts of heavier hydrocarbons which are ultimately removed from the fractionation zone as part of the bottoms stream.

The fractionation zone including the trays and reboilers, the condensers, control valves, compressors, temperature and pressure sensors and other apparatus required to practice the subject invention may be of customary design. It is believed well within the expertise of those skilled in the arts of fractionation and process design to specify suitable equipment.

The subject process utilizes a heat pump. These devices function by compressing a vapor stream, an action which in accordance with the laws of thermodynamics increases the temperature of the vapor stream. The vapor stream may then be heat exchanged against an object which it is desired to heat. The effect of the heat pump is to establish a thermal gradient which allows practical heat transfer at the expense of mechanical energy. Heat pumps therefore allow heat to be added to or removed from a system by the application of mechanical energy to a circulating working stream. In some situations, the use of heat pumps is more energy-efficient than other methods. This has been recognized in the art as shown by the increased usage and attention being given to heat pumps in such diverse areas as fractionation and residential air conditioning and heating.

Heat pumps have been used in what is referred to herein as the conventional manner to improve the energy-efficiency of fractionation systems. The previously cited prior art illustrates these conventional heat pump systems in which warm overhead vapors are compressed and thereby heated to a temperature sufficient for use in the reboiler system. The hot vapors are then indirectly heat exchanged with the bottoms liquid to be vaporized. In most cases, the hot overhead vapor stream is simultaneously condensed to form a liquid which is then used as reflux and also withdrawn as the overhead product.

In the subject process, an overhead vapor stream is removed from the top of a fractionation zone, which preferably comprises a single trayed column but which may also comprise two or more interconnected columns. As used herein, the term "overhead vapor stream" is intended to indicate the vapor stream flowing from the column to the overhead receiver. A different vapor stream referred to herein as the receiver vapor stream is withdrawn from the overhead receiver.

The receiver vapor stream is superheated by indirect heat exchange to prevent condensation within the compressor utilized as the heat pump. The thus-heated receiver vapor stream is then further heated in the compressor. The twice-heated vapor stream which is discharged from the compressor is referred to herein as the high pressure working stream. The high pressure working stream is cooled by indirect heat exchange against the receiver vapor stream in the same exchanger in which the receiver vapor stream is heated. That is, the feed and effluent streams of the compressor are heat exchanged against each other. A relatively small amount of the high pressure working stream may, if desired, be returned to the overhead receiver through a spillback line provided for this purpose. This small stream preferably constitutes 10 percent or less of the total high pressure working stream and is maintained to improve the controllability of the flow control valves used in the control system.

The major flow of the high pressure working stream is divided into two portions, both of which are ultimately subcooled in the preferred embodiment of the invention. A first portion of the high pressure working stream is passed through a reboiler which supplies heat to the fractionation zone at an intermediate point located below the feed point. As used herein, the term "intermediate point" is intended to indicate a location which is separated from both ends of the fractionation zone by at least two fractionation trays or amount of other contacting material equal to one theoretical contacting stage. The effluent of this intermediate reboiler will normally be a mixed phase stream and is preferably passed directly into an air-cooled condenser wherein it is subcooled. The flow rate of the first portion of the high pressure working stream is controlled by a valve regulating the flow of the condenser effluent. The cool liquid phase condenser effluent stream is then passed into the overhead receiver to achieve direct heat exchange with the overhead vapor stream.

A second portion of the high pressure working stream is passed directly into a second condenser, which is often referred to as the trim condenser of the system. The flow rate of the second portion of the high pressure working stream is also controlled by a valve regulating the flow of the condenser effluent. The set point of the controller which adjusts the opening of this valve is periodically adjusted as required to maintain the desired pressure within the overhead receiver and the fractionation zone. For instance, if the pressure within the system begins to climb above an acceptable value, the pressure controller monitoring this pressure will raise the setpoint of the flow control valve. This will increase the flow rate of the relatively cool trim condenser effluent stream. This in turn increases the flow of cool liquid into the overhead receiver, and a greater amount of the overhead vapor stream is condensed. This lowers the pressure in the overhead receiver and in the fractionation zone. A pressure decrease within the column causes the reverse of this sequence to occur. The trim condenser is also used during startup to generate reflux liquid.

Preferably, a portion of the subcooled effluent of the trim condenser is removed from the process as the net overhead product stream. The remainder of the trim condenser effluent is passed into the overhead receiver. In another embodiment of the invention, a portion of the liquid withdrawn from the overhead receiver is removed from the process as the net overhead product stream. In either embodiment, the rate of flow of the overhead product stream is regulated by a valve which is adjusted in accordance with a temperature controller which monitors a temperature within an upper section of the fractionation zone. For instance, if the temperature within the upper section of the fractionation zone begins to rise above a preselected desired temperature, then the temperature controller sends a signal which decreases the flow rate of the overhead product stream. This flow rate change is accomplished by adjusting the setpoint of the flow controller which adjusts the opening of the valve through which the overhead product stream flows. A decrease in the rate of overhead product removal causes liquid to accumulate in the overhead receiver. The liquid level in the receiver therefore increases. The level controller which monitors this level senses this increased level and sends a signal to the flow controller which adjusts the valve through which the reflux liquid is passed into the fractionation zone. This signal is one which results in the valve opening to a greater extent and which thereby increases the flow of reflux liquid to the column. This lowers the temperature of the fluids in the upper section of the column. The reverse of this sequence occurs if the column top temperature decreases below the preselected desired temperature. In practice, the overhead product stream is withdrawn at only one point, with the other flow control valve being entirely closed.

The following example, which is based on a proposed commercial installation, illustrates the use of the subject process. It is based on a butane isomerization unit similar to that shown in the drawing, and reference will occasionally be made to the numerals used in the drawing to clarify the particular stream or apparatus being described. The n-butane fresh feed stream of line 1 has a flow rate of about 2062 mph (moles per hour). This stream is dried and passed through the reactor section of the catalytic isomerization zone in admixture with hydrogen and the recycle stream of line 6. The very great majority of the $C_4$ hydrocarbons in the effluent of the reactor section are condensed, separated from the remaining vapor and passed into a stripping (stabilizer) column. The net bottoms stream of this stripping column is passed into the butane splitter column 5 through line 4. This stream has a flow rate of about 4150 mph and contains 47.1 mol.% isobutane, 49.1 mol.% normal butane and 3.8 mol.% pentanes. The overhead vapor stream removed from the column has a flow rate of approximately 17,900 mph, a temperature of about 53° C. and a pressure of about 91 psig. The overhead receiver vapor stream of line 26 has a flow rate of approximately 20,170 mph, a temperature of about 53° C. and a pressure of about 91 psig. The receiver vapor stream is heated to about 57° C. by indirect heat exchange and then compressed to 216 psig. in the compressor 29. The high pressure working stream (compressor effluent stream) has a temperature of about 91° C. and is then cooled to approximately 88° C. by heat exchange against the receiver vapor stream.

About 1980 mph of the high pressure working stream is allowed to spill back to the overhead receiver in line 12. A first large portion of the high pressure working stream having a flow rate of about 16,040 mph is passed into the upper reboiler 34. This portion of the high pressure working stream emerges from the upper reboiler as a condensate stream and is subcooled below its bubble point in the air-cooled cooler 56. The effluent of the cooler 56 has a temperature of about 52° C. and a pressure of about 195 psig. This cool liquid is depressurized and passed into the overhead receiver. About 98 million BTU per hour of heat is provided to the column in the upper reboiler.

A second portion of the high pressure working stream is passed into the trim condenser 40 at a flow rate of about 2160 mph and a temperature of about 88° C. The effluent of the trim condenser has a temperature of about 53° C. Approximately 1880 mph of the trim condenser effluent is removed in line 42 as the net overhead product of the fractionation column. The overhead product is about 97 mol.% isobutane and 3 mol.% normal butane. The remainder of the trim condenser effluent is depressurized and passed into the overhead receiver.

The fractionation column contains 80 trays above the upper reboiler, with there being a total trap out of the descending liquid into the reboiler tub surrounding the upper reboiler. A recycle sidecut stream is withdrawn from the column and passed into the isomerization zone. This sidecut stream has a flow rate of approximately 2200 mph and a temperature of about 68° C. Liquid overflow from the reboiler tub enters the portion of the column below the upper reboiler. This part of the column contains ten additional trays. A net bottoms stream having a flow rate of approximately 68 mph is removed in line 53. This stream contains approximately 1 mol.% isobutane, 72 mol.% normal butane and 27 mol.% iso and normal pentanes. The heat input to the column via the bottom reboiler is about 30 million BTU per hour or approximately 24% of the total heat input to the column supplied by the two reboilers. It must be understood that these flow rates and conditions are only representative of ideal steady state operation and that the actual operating conditions will vary depending on a great many variables ranging from the ambient atmospheric temperature to the conversion rate achieved in the isomerization zone.

In accordance with the above example, one embodiment of the invention may be characterized as a process for recovering the product hydrocarbon of an isomerization reaction by fractional distillation which comprises the steps of passing a fractionation feed stream comprising two isomeric hydrocarbons and which is derived from the vaporous effluent of an isomerization zone into a fractionation zone operated at fractionation conditions at a first intermediate point; removing a net bottoms stream which is rich in a first hydrocarbon from the fractionation zone as a first product stream; removing an overhead vapor stream which is rich in a second hydrocarbon which is the more volatile of two isomeric hydrocarbon present in the feed stream from the fractionation zone and partially condensing the overhead vapor stream by direct heat exchange within an overhead receiver to produce an overhead liquid and a receiver vapor stream, and supplying a portion of the overhead liquid to the fractionation zone as reflux; heating the receiver vapor stream by indirect heat exchange against a hereinafter specified high pressure working stream; heating the receiver vapor stream by compression and thereby forming the previously specified high pressure working stream; cooling the high pressure working stream by indirect heat exchange against the overhead vapor; passing a first portion of the high pressure working stream through a first reboiler which is used to supply heat to the fractionation zone at a second intermediate point located below the first intermediate point, condensing the high pressure working stream to thereby form a liquid hydrocarbon stream, and then passing the liquid hydrocarbon stream into the overhead receiver; condensing and subcooling a second portion of the high pressure working stream to thereby form a condensate stream, passing a first portion of the condensate stream into the overhead receiver and removing a second portion of the condensate stream as a second product stream; and supplying heat to the bottom of the fractionation zone through the use of a lower second reboiler.

Any reference herein to a stream as being rich in a particular compound is intended to indicate that over 70 mol.% of the stream is made up of the particular compound. In a similar manner, referring to a stream as substantially pure is intended to indicate it contains over 98 mol.% of the indicated compound. These relative terms are necessary because of the minor amounts of contaminants which are commonly found in industrial grade chemical streams. This is in keeping with the common knowledge of those skilled in the art that it is often commercially impractical to utilize or produce process streams which are pure in the true sense of the word. Nevertheless, it is preferred that both the overhead and bottoms product streams produced in the subject process are substantially pure streams of a single compound.

I claim as my invention:

1. A process for separating two chemical compounds by fractionation which comprises the steps of:
    (a) passing a feed stream comprising a first and a second chemical compound into a fractionation zone operated at fractionation conditions;
    (b) removing a net bottoms stream which is rich in the first chemical compound from the fractionation zone as a first product stream;
    (c) removing an overhead vapor stream which is rich in the second chemical compound from the fractionation zone, partially condensing the overhead vapor stream by direct heat exchange within an overhead receiver to produce an overhead liquid and a receiver vapor stream, supplying a first portion of the overhead liquid to the fractionation zone as reflux and removing a second portion of the overhead liquid from the process as a second product stream;
    (d) heating the receiver vapor stream by indirect heat exchange against a hereinafter specified high pressure working stream;
    (e) heating the receiver vapor stream by compression and thereby forming the previously specified high pressure working stream;
    (f) cooling the high pressure working stream by indirect heat exchange against the receiver vapor stream;
    (g) passing a first portion of the high pressure working stream through a first reboiler which is used to supply heat to the fractionation zone and then into the overhead receiver; and,
    (h) condensing a second portion of the high pressure working stream to thereby form a condensate stream and then passing the resultant condensate stream into the overhead receiver.

2. The process of claim 1 further characterized in that the first and the second chemical compounds are hydrocarbons.

3. The process of claim 2 further characterized in that the hydrocarbons have less than seven carbon atoms per molecule.

4. The process of claim 3 further characterized in that the first reboiler is located at an intermediate point below the point at which said feed stream enters the fractionation zone and in that a second reboiler is utilized to supply heat to the fractionation zone at a location below the first reboiler.

5. The process of claim 4 further characterized in that the hydrocarbons have three or four carbon atoms per molecule.

6. A process for separating two chemical compounds by fractionation which comprises the steps of:
    (a) passing a feed stream comprising a first and a second chemical compound into a fractionation zone operated at fractionation conditions;
    (b) removing a net bottoms stream which is rich in the first chemical compound from the fractionation zone;
    (c) removing an overhead vapor stream which is rich in the second chemical compound from the fractionation zone, partially condensing the overhead vapor stream by direct heat exchange within an overhead receiver to produce an overhead liquid and a receiver vapor stream, and supplying the overhead liquid to the fractionation zone as reflux;
    (d) heating the receiver vapor stream by indirect heat exchange against a hereinafter specified high pressure working stream;
    (e) heating the receiver vapor stream by compression and thereby forming the previously specified high pressure working stream;
    (f) cooling the high pressure working stream by indirect heat exchange against the receiver vapor stream;
    (g) passing a first portion of the high pressure working stream through a first reboiler which is used to supply heat to the fractionation zone and then into the overhead receiver;

(h) condensing a second portion of the high pressure working stream to thereby form a condensate stream; and, (i) passing a first portion of the condensate stream into the overhead receiver and removing a second portion of the condensate stream from the process as a second product stream which is rich in the second chemical compound.

7. The process of claim 6 further characterized in that the first and the second chemical compounds are hydrocarbons.

8. The process of claim 7 further characterized in that the hydrocarbons have less than seven carbon atoms per molecule.

9. The process of claim 8 further characterized in that the first reboiler is located at an intermediate point below the point at which the feed stream enters the fractionation zone and in that a second reboiler is utilized to supply heat to the fractionation zone at a location below the first reboiler.

10. The process of claim 9 further characterized in that the hydrocarbons have three or four carbon atoms per molecule.

11. A process for recovering the product hydrocarbon of an isomerization reaction by fractional distillation which comprises the steps of:

(a) passing a fractionation zone feed stream comprising two isomeric hydrocarbons and which is derived from the vaporous effluent of an isomerization zone into a fractionation zone operated at fractionation conditions at a first intermediate point;

(b) removing a net bottoms stream which is rich in a first hydrocarbon from the fractionation zone as a first product stream;

(c) removing an overhead vapor stream which is rich in a second hydrocarbon, which is the more volatile of two isomeric hydrocarbons present in the feed stream, from the fractionation zone and partially condensing the overhead vapor stream by direct heat exchange within an overhead receiver to produce an overhead liquid and a receiver vapor stream, and supplying a portion of the overhead liquid to the fractionation zone as reflux;

(d) heating the receiver vapor stream by indirect heat exchange against a hereinafter specified high pressure working stream;

(e) heating the receiver vapor stream by compression and thereby forming the previously specified high pressure working stream;

(f) cooling the high pressure working stream by indirect heat exchange against the overhead vapor;

(g) passing a first portion of the high pressure working stream through a first reboiler which is used to supply heat to the fractionation zone at a second intermediate point located below the first intermediate point, condensing the high pressure working stream to thereby form a liquid hydrocarbon stream, and then passing the liquid hydrocarbon stream into the overhead receiver;

(h) condensing and subcooling a second portion of the high pressure working stream to thereby form a condensate stream, passing a first portion of the condensate stream into the overhead receiver and removing a second portion of the condensate stream as a second product stream; and, (i) supplying heat to the bottom of the fractionation zone through the use of a lower second reboiler.

12. The process of claim 11 further characterized in that a sidecut stream is removed from the fractionation zone at a location which is below the first intermediate point but not below the first reboiler, and in that the sidecut stream is passed into the isomerization zone as at least a portion of the feed stream of the isomerization zone.

13. The process of claim 11 further characterized in that the isomeric hydrocarbons have three or four carbon atoms per molecule.

14. The process of claim 11 further characterized in that the second hydrocarbon is isobutane.

* * * * *